United States Patent
Galletti et al.

(10) Patent No.: US 6,368,559 B1
(45) Date of Patent: Apr. 9, 2002

(54) DEVICE FOR ANALYZING ORGANIC COMPOUNDS PARTICULARLY IN AQUEOUS AND GASEOUS SAMPLES

(75) Inventors: Guido Galletti, Misano Adriatico; Paola Bocchini, Cesena, both of (IT)

(73) Assignee: Universita' Degli Studi di Bologna, Bologna (IT)

(*) Notice: Subject to any disclaimer, the term of this patent is extended or adjusted under 35 U.S.C. 154(b) by 0 days.

(21) Appl. No.: 09/586,888

(22) Filed: Jun. 5, 2000

(30) Foreign Application Priority Data

Jun. 24, 1999 (IT) .......................... B099A0345

(51) Int. Cl.[7] .................. G01N 30/96; G01N 33/48
(52) U.S. Cl. .................. 422/69; 422/68.1; 422/70; 422/83; 422/88; 422/89; 422/101; 73/863.12; 73/23.39; 73/23.35; 436/178; 95/87; 95/88; 96/104
(58) Field of Search .................. 422/69, 68.1, 70, 422/83, 88, 89, 101; 250/288, 281; 73/863.12, 864.81, 23.39, 23.35; 436/173, 178; 95/87, 88; 96/103, 104

(56) References Cited

U.S. PATENT DOCUMENTS

| | | | | |
|---|---|---|---|---|
| 4,328,677 A | * | 5/1982 | Meckler | 62/124 |
| 4,891,968 A | * | 1/1990 | Steudle et al. | 73/64.3 |
| 5,014,541 A | * | 5/1991 | Sides et al. | 73/23.41 |
| 5,142,143 A | * | 8/1992 | Fite et al. | 250/288 |
| 5,149,661 A | * | 9/1992 | Gjerde et al. | 436/178 |
| 5,492,838 A | * | 2/1996 | Pawliszyn | 436/178 |
| 5,639,375 A | * | 6/1997 | Hiroshi | 210/640 |
| 5,679,576 A | * | 10/1997 | Kawal et al. | 436/55 |
| 5,922,106 A | * | 7/1999 | Mowry et al. | 95/87 |
| 5,929,321 A | * | 7/1999 | Bertrand | 73/23.39 |
| 6,143,568 A | * | 11/2000 | Pilz | 436/62 |

* cited by examiner

Primary Examiner—Jill Warden
Assistant Examiner—Brian Sines
(74) Attorney, Agent, or Firm—Guido Modiano; Albert Josif; Daniel O'Byrne

(57) ABSTRACT

A device for analyzing organic compounds, particularly in aqueous and gaseous samples, constituted by a duct which is supplied in input by a gas whose pressure can be controlled by means of a regulator connected to a capillary column which is connected in output to a detector for the organic compounds; an adsorbent polymer immersed in a container is interposed between a first portion and a second portion of the capillary column, and the device comprises, between the second portion and a third portion, means for concentrating the organic compounds; the container contains an aqueous or gaseous sample which interacts with the adsorbent polymer adapted to extract the organic compounds conveyed by the gas in passing through the adsorbent polymer toward the concentration means in order to be measured by the detector.

5 Claims, 2 Drawing Sheets

DEVICE FOR ANALYZING ORGANIC COMPOUNDS PARTICULARLY IN AQUEOUS AND GASEOUS SAMPLES

BACKGROUND OF THE INVENTION

A problem that is currently strongly felt is due to the pollution of water and air caused by the presence of organic compounds which may have various origins. For example, some of them, such as trihalomethanes (chloroform, bromoform, dibromochloromethane, dichlorobromomethane), derive from disinfectant treatments consisting of water chlorination, while other compounds, such as carbon tetrachloride, trichloroethane, trichloroethylene and tetrachloroethylene, derive from industrial and domestic emissions of various chlorinated solvents into the environment.

It is known that various devices for detecting organic compounds present in water and gases at very low concentration are currently commercially available and in use.

Some of these devices, although allowing to reach low limits of organic compound detectability, have problems linked to the steps for pre-treatment of the sample, such as extraction, concentration and purification, which considerably increase the analysis times and are costly. Another problem is due to the fact that they do not allow to perform continuous analysis on the samples.

Other devices, instead, such as the one known as MIMS (Membrane Introduction Mass Spectrometry), are constituted by a capillary element which is connected in series to a hollow-fiber polymer membrane inserted in a mass spectrometer.

A problem that is often noted in this kind of device is the fact that the sample, by flowing inside the membrane, causes it to clog and/or break and causes the sample to leak into the mass spectrometer, with very severe consequences for the apparatus.

Another problem that is strongly felt in this type of device is the noise that affects the measurement signal: the measurement signal-to-noise ratio is in fact very small.

The aim of the present invention is to eliminate the drawbacks noted above by providing a device for analyzing organic compounds in which, while using simple instruments, it is possible to achieve high detectability of the organic compounds present in aqueous and gaseous samples, with a more advantageous ratio between the measurement signal and the noise.

Within the scope of this aim, an object of the present invention is to provide a device in which extraction, concentration and introduction of the organic compounds in the mass spectrometer occur in a single stage, thus reducing analysis times.

Another object of the present invention is to provide the capability to perform analyses on aqueous and gaseous samples both in a continuous stream and in discrete samples.

Another object of the present invention is to be able to perform organic compound detectability analyses both in the laboratory and on the spot.

Another object of the present invention is to provide a device which is easy to provide in practice and can be obtained starting from commonly commercially available elements and materials.

BRIEF DESCRIPTION OF THE INVENTION

This aim, these objects and others which will become better apparent hereinafter are achieved by a device for analyzing organic compounds, particularly in aqueous and gaseous samples, which comprises a duct which is supplied in input by a gas whose pressure can be controlled by means of a regulator connected to a capillary column which is connected in output to a detector for said organic compounds, an adsorbent polymer immersed in a container being interposed between a first portion and a second portion of said capillary column, characterized in that it comprises, between said second portion and a third portion, means for concentrating said organic compounds, said container containing an aqueous or gaseous sample which interacts with said adsorbent polymer adapted to extract said organic compounds conveyed by said gas in passing through said adsorbent polymer toward said concentration means in order to be measured by said detector.

DETAILED DESCRIPTION OF THE INVENTION

Further characteristics and advantages of the present invention will become better apparent from the following detailed description of a preferred but not exclusive embodiment of a device for analyzing organic compounds, particularly in aqueous and gaseous samples, according to the invention, illustrated only by way of non-limitative example in the accompanying drawings, wherein.

DESCRIPTION OF THE PREFERRED EMBODIMENTS

Figure 1:
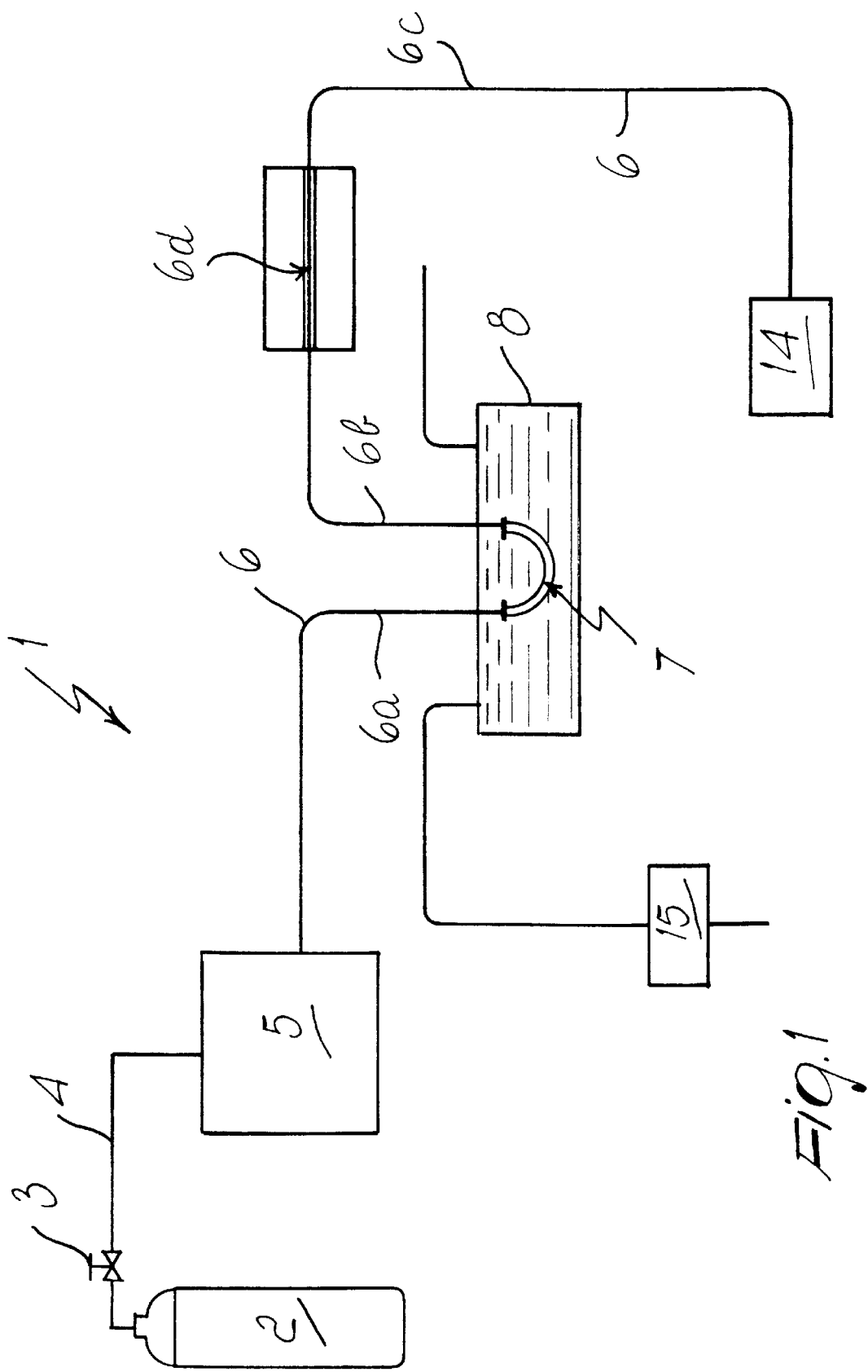
FIG. 1 is a layout of the device according to the present invention.

With reference to FIG. 1, 1 generally designates the layout of a device for analyzing organic compounds, particularly in aqueous and gaseous samples. The layout 1 is constituted by a cylinder 2 which contains a gas, for example helium. The cylinder 2 is connected, at a flow regulator valve 3, to the input of a duct 4 which is connected in output to a regulator 5. The regulator 5 is connected to a capillary column 6 which has a hollow circular cross-section and has, between a first portion 6a and a second portion 6b, an adsorbent polymer 7 which is immersed in a container 8 and accommodates aqueous or gaseous samples.

Figure 2:
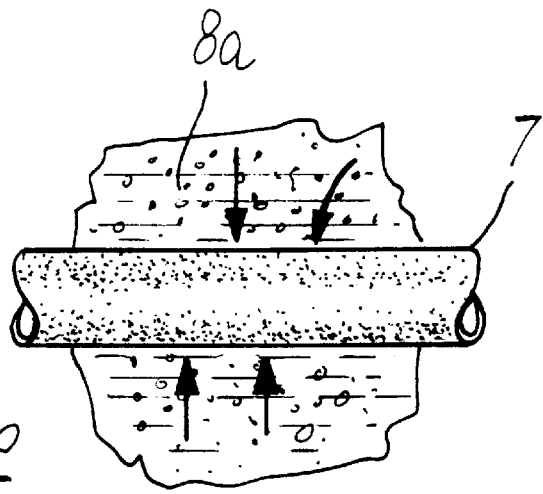
FIG. 2 is an enlarged-scale view of a detail of the device.

The adsorbent polymer 7, see FIG. 2, is provided by a membrane made of hydrophobic hollow fiber which is impermeable to polar substances, such as water, and permeable to nonpolar substances, such as the organic compounds 8a, which are adsorbed by the adsorbent polymer 7, diffuse inside the capillary column 6 and are conveyed by the gas arriving from the cylinder 2.

Figure 3:
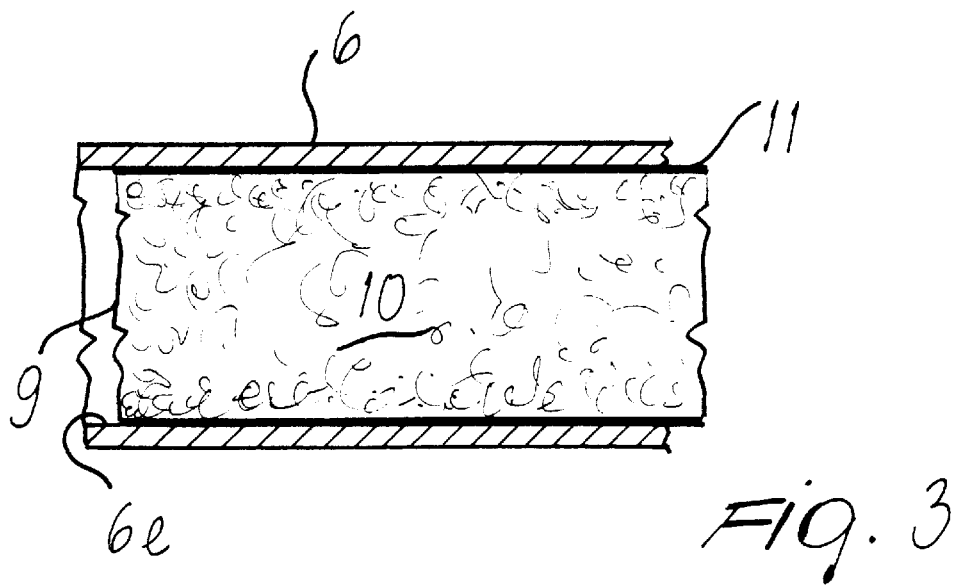
FIG. 3 is an enlarged-scale sectional view of another detail of the device.

Between the second portion 6b and the third portion 6c there is a region 6d which internally accommodates concentration means 9. Said concentration means 9 (see FIG. 3) comprise an adsorbent element 10, constituted by a portion of polymeric material, such as for example a material known commercially by the name Tenax. Advantageously, the internal wall 6e of a portion of the capillary column 6 which lies between the second portion 6b, the third portion 6c and the region 6d can be covered on its surface by a film 11 which retains the impurities of the organic compounds 8a that arrive from the adsorbent polymer 7.

Figure 4:
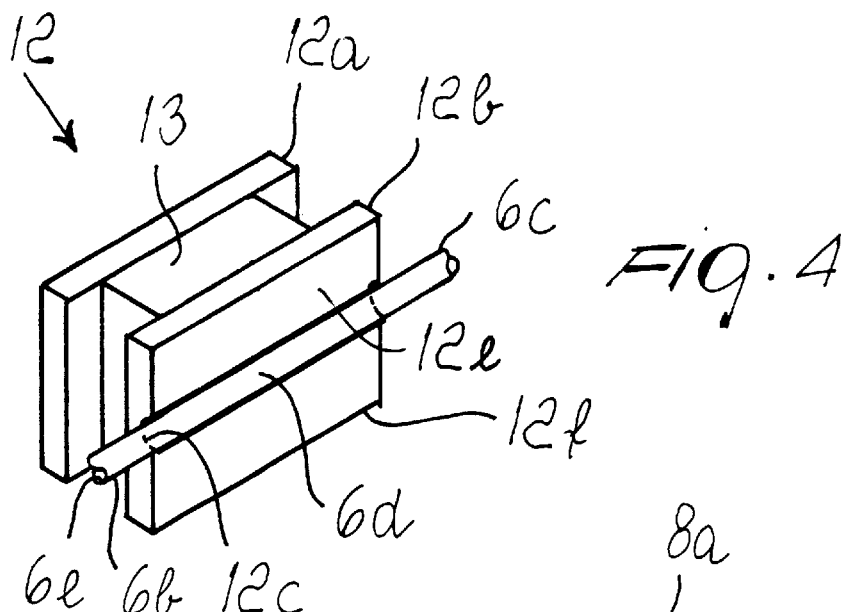
FIG. 4 is a perspective view of a heat exchanger.

The region 6d is thermally coupled to a heat exchanger 12 (see FIG. 4) constituted by a pair of laminas 12a and 12b which accommodate the region 6d in a slot 12c which is formed on an outer face 12e and is parallel to a longer side 12f of the lamina 12b. Moreover, the two laminas 12a, 12b are coupled to a Peltier cell 13 which, during the cooling step, facilitates the entrapment of the organic compounds 8a in the adsorbent element 10 and, during the heating step, facilitates desorption of the organic compounds 8a toward a detector 14 preferably constituted by a mass spectrometer.

The container 8 comprises, in one embodiment, a glass jacket which is connected to a peristaltic pump 15 which continuously feeds the aqueous or gaseous sample to be analyzed. In another embodiment, the container 8 is constituted by a flask, and in this case analysis is not continuous but proceeds by discrete samples.

Initially, the pressure of the gas, for example helium, is reduced by means of the regulator valve 3 and is then finely adjusted by the regulator 5, so that the pressure drop in the capillary column 6, made of melted silica with no stationary phase and having advantageous dimensions, is compatible with the correct operating pressure of the mass spectrometer.

Advantageously, the gas pressure regulator 5 can be constituted by a commercial gas chromatograph, thus allowing to easily integrate the device with common gas chromatographs/mass spectrometers.

When the sample of organic compounds 8a, contained in the container 8, contacts the adsorbent polymer 7, said compounds are adsorbed thereon and, by then penetrating it, are drawn inside the capillary column 6 toward the mass spectrometer. Before the mass spectrometer, the concentration means 9, by means of the adsorbent element 10, trap the organic compounds 8a. The entrapment or concentration of the organic compounds 8a in the adsorbent element 10 is facilitated by the presence of the heat exchanger 12 coupled to the Peltier cell 13. Initially, in fact, by means of the Peltier cell 13 it is possible to provide cooling, for example for 5–10 minutes and to values between 0 and −30° C., enhancing the organic compound adsorption capacity of the adsorbent element, constituted by the known commercial material Tenax; then, by means of the Peltier cell 13, by rapidly raising the temperature, for example to 100–150° C. in approximately one minute, the organic compounds 8a concentrated in large amounts in the adsorbent element 10 are desorbed and sent to the mass spectrometer. In this way it is possible to send to the mass spectrometer, in a very short time, even small traces of organic compounds present in the aqueous solution, allowing a high measurement signal/noise ratio and accordingly a low limit of detectability.

Moreover, the advantageous presence of the film 11 in the portion of the capillary column 6 that lies between the second portion 6b, the third portion 6c and the region 6d allows to retain the impurities that are present in the organic compounds that reach the mass spectrometer or also to obtain separate measurements for the organic compounds 8a.

From the above description it is evident that the invention achieves the intended aim and objects, and in particular the fact is stressed that the analysis of the aqueous solution requires no pre-treatments, thus allowing short analysis times.

The invention thus conceived is susceptible of numerous modifications and variations, all of which are within the scope of the inventive concept.

All the details may further be replaced with other technically equivalent ones.

In practice, the materials used, as well as the shapes and the dimensions, may be any according to requirements without thereby abandoning the scope of the appended claims.

The disclosures in Italian Patent Application No. BO99A000345 from which this application claims priority are incorporated herein by reference.

What is claimed is:

1. A device for analyzing organic compounds, particularly in aqueous and gaseous samples, comprising:
   a gas supply;
   a duct connected in input at the gas supply and in output to a gas pressure regulator;
   a capillary column connected to the regulator and having a first, a second and a third portion, and a region that lies between said second portion and said third portion;
   an adsorbent polymer located between the first and the second portion of the capillary column;
   concentration means for concentration of the organic compounds, located between the second and the third portion of the capillary column and comprising an adsorbent element which is accommodated internally in said region of the capillary column;
   a heat exchanger thermally coupled to said region of the capillary column and adapted to facilitate entrapment of said organic compounds during cooling and to facilitate desorption of said entrapped organic compounds during heating, the heat exchanger being constituted by two laminas which accommodates said region of the capillary column in a slot, said two laminas being coupled to a Peltier cell;
   a detector for detecting the organic compounds, connected at the output of the capillary column; and
   a container for containing a sample of organic compound to be analyzed by immersion of the adsorbent polymer in the container thereby the organic compound being extracted by the adsorbent polymer and conveyed by gas from the gas supply passing through said adsorbent polymer towards the concentration means and the detector.

2. The device according to claim 1, further comprising a film which lines the internal wall of said region and said second and third portions, said film being adapted to retain impurities present in said organic compounds.

3. The device according claim 1, further comprising a pump which is connected to said container and is adapted to continuously feed said aqueous or gaseous sample to be analyzed.

4. The device according to claim 1, wherein said adsorbent element is constituted by hollow-fiber polymeric material.

5. The device according to claim 1, wherein said detector is a mass spectrometer.

* * * * *